United States Patent [19]

Bito et al.

[11] Patent Number: 4,952,581
[45] Date of Patent: Aug. 28, 1990

[54] USE OF A PROSTAGLANDIN IN COMBINATION WITH AN ADRENERGIC BLOCKING AGENT FOR REDUCTION OF INTRAOCULAR PRESSURE

[75] Inventors: Laszlo Z. Bito, New York, N.Y.; Johan W. Stjernschantz, Uppsala, Sweden

[73] Assignee: The Trustees of Columbia University in the City of New York, New York, N.Y.

[21] Appl. No.: 292,321

[22] Filed: Dec. 30, 1988

Related U.S. Application Data

[63] Continuation of Ser. No. 34,484, Apr. 3, 1987, abandoned.

[51] Int. Cl.$^5$ ............... A61K 31/535; A61K 31/215; A61K 31/19
[52] U.S. Cl. ............................... 514/236.2; 514/530; 514/573; 514/913
[58] Field of Search ................ 514/530, 573, 913

[56] References Cited

U.S. PATENT DOCUMENTS 4,474,751 10/1984 Haslam et al. ............... 514/171
4,599,353 7/1986 Bito ............................... 514/530

*Primary Examiner*—Douglas W. Robinson
*Assistant Examiner*—Zohreh A. Fay
*Attorney, Agent, or Firm*—John P. White

[57] ABSTRACT

This invention provides a method for treating ocular hypertension or glaucoma in a subject's eye. The method comprises contacting the surface of the eye with an effective intraocular pressure reducing amount of a mixture of an adrenergic blocking agent and a prostaglandin or prostaglandin derivative in an ophthalmically compatible carrier, so as to reduce the intraocular pressure of the eye and maintain such reduced intraocular pressure.

This invention also provides a composition for topical treatment of ocular hypertension or glaucoma in the eye of a subject. The composition comprises an effective intraocular pressure reducing amount of a mixture of an adrenergic block agent and a prostaglandin or prostaglandin derivative in an ophthalmically compatible carrier.

23 Claims, 4 Drawing Sheets

USE OF A PROSTAGLANDIN IN COMBINATION WITH AN ADRENERGIC BLOCKING AGENT FOR REDUCTION OF INTRAOCULAR PRESSURE

BACKGROUND OF THE INVENTION

The invention described herein was made with government support under grant number EY00333 from the National Eye Institute, National Institutes of Health, Department of Health and Human Services. The U.S. Government has certain rights in this invention.

This application is a continuation of U.S. Ser. No. 034,484, filed Apr. 3, 1987, now abandoned.

Glaucoma, an eye disorder afflicting various mammals, including primates, is characterized by increased intraocular pressure (ocular hypertension). In man, such ocular hypertension results from an imbalance between the rate of secretion of aqueous humor by the ciliary epithelium into the posterior chamber of the eye and the resistance drainage of the aqueous humor from the anterior chamber, primarily via the canal of Schlemm. It is generally believed that increased outflow resistance due to obstruction of aqueous humor drainage routes is the primary cause of the imbalance.

Chronic glaucoma typically results in slow, progressive loss of visual fields and, if not controlled, ultimately in blindness. Initial treatment usually involves topical application of agonists or antagonists of autonomic neuroeffectors, particularly pilocarpine or timolol. If treatment with such topically applied drugs is not effective, systemic administration of carbonic anhydrase inhibitors may be employed. If such approaches are unsuccessful, the glaucoma may have to be treated by surgery or laser. Eicosanoids and their derivatives include numerous biologically useful compounds. For example, the prostaglandin (PG) group, naturally occurring cyclic fatty acids, is known to possess diverse biological activities. Originally isolated as lipid-soluble extracts from sheep seminal vesicles and human seminal fluid, prostaglandins have been found to be produced by most mammalian tissues.

Activities of different prostaglandins include stimulation or relaxation of smooth muscle, dilation of small arteries, bronchial dilation, lowering of blood pressure, inhibition of gastric secretion, lipolysis and platelet aggregation, and induction of labor, abortion and menstruation.

It is becoming increasingly evident that PGs reduce intraocular pressure by increasing uveoscleral outflow. This is true for both the F type and A type of PGs and, hence presumably also for the E and B type PGs. See also, U.S. Pat. No. 4,599,353, issued Jul. 8, 1986, and co-pending, U.S. patent application, Ser. No. 839,056, filed Mar. 13, 1986, the contents of which are hereby incorporated by reference into this application. Contraction of the ciliary muscle as induced by pilocarpine, for example, reduces or blocks uveoscleral outflow while uveoscleral outflow may be assumed to be increased by relaxation of the ciliary muscle. This is because the pathway of uveoscleral outflow is through the muscle part of the ciliary body, i.e., relaxation of the muscle increases the extracellular space between muscle fibers in this tissue, whereas contraction of the muscle decreases this space, thus decreasing or eliminating this flow pathway. PGs could relax the ciliary muscle by one of two mechanisms: either by causing the release of catecholamines from adrenergic nerve endings contained within the ciliary muscle; or by acting on the ciliary muscle directly, causing relaxation by interaction with PG receptors of the muscle fiber surface. In the former case, adrenergic blocking agents, particularly beta blockers, would block the PG-induced increase in uveoscleral outflow. In the latter case, beta blockers would not block the beneficial intraocular pressure reducing effects of PGs.

Therefore, if topically applied, PGs would reduce intraocular pressure by relaxing the ciliary muscle through the release of catecholamines; combined therapy of an adrenergic blocking agent and PGs would be counterproductive since the adrenergic blocking agent would block the ocular hypotensive effect of the PG. However, if PGs acted directly on the ciliary muscle without the mediation of catecholamines, than adrenergic blocking agents would not interfere with the ocular hypotensive effect of PGs.

The most effective way of reducing intraocular pressure is by affecting both sides of the pressure equation: $P = F \times R$; where R is the resistance to the outflow of aqueous humor, F is flow (which, in turn, equals the rate of secretion of aqueous humor) and P equals the effective pressure gradient across the site of resistance (namely, intraocular pressure—episcleral venous pressure). According to currently accepted concepts, there are two sites of aqueous humor outflow from the eye; the conventional outflow through the trabecular meshwork and the above-mentioned uveoscleral flow through the ciliary muscles. Pilocarpine decreases the resistance in the conventional flow channels through the trabecular meshwork; therefore, it works effectively in combination with an adrenergic blocking agent. However, pilocarpine at the same time decreases uveoscleral outflow by contracting the ciliary muscle. In some cases of glaucoma, when flow through the trabecular meshwork is reduced to the point when it cannot be effectively increased by pilocarpine, pilocarpine can have only a very small additional beneficial effect or may have an adverse rather than a beneficial effect by reducing the remaining outflow channels through the ciliary muscle. Therefore, a combination drug, or drug regimen, that acts by decreasing aqueous humor secretion, such as an adrenergic blocking agent and a PG would be ideal, provided that the adrenergic blocking agent can be shown not to block the ocular hypotensive effects of PGs.

In the medical treatment of glaucoma, combination therapy, therefore, is commonly required since in many cases effective intraocular pressure control cannot be maintained with a single drug. The experiments set forth herein establish that the use of a combination of an adrenergic blocking agent and a PG have a great advantage from a physiological point of view, since they show that adrenergic blocking agents do not block the ocular hypotensive effect of a PG and since these blocking agents act by reducing the secretion of aqueous humor whereas PGs, as stated above, act by increasing uveoscleral outflow. In addition, using a combination of an adrenergic blocking agent and a prostaglandin, each of them in a concentration lower than would be required if used separately in the treatment of ocular hypertension and glaucoma, would yield a significant reduction in the occurrence of such side effects as ocular discomfort, irritative responses, conjunctival hyperemia, and cardiovascular response.

SUMMARY OF THE INVENTION

This invention provides a method for treating ocular hypertension or glaucoma in a subject's eye. The method comprises contacting the surface of the eye with a composition comprising an effective intraocular pressure reducing amount of a mixture of an adrenergic blocking agent and a prostaglandin or prostaglandin derivative in an ophthalmically compatible carrier, so as to reduce the intraocular pressure of the eye and maintain such reduced intraocular pressure.

The invention also provides a composition for topical treatment of ocular hypertension or glaucoma. The composition comprises an effective intraocular pressure reducing amount of a mixture of an adrenergic blocking agent and a prostaglandin or prostaglandin derivative in an ophthalmically compatible carrier.

Moreover, this invention provides a method for treating ocular hypertension or glaucoma in a primate subject's eye which comprises contacting the surface of the eye with a composition comprising an effective intraocular pressure reducing amount of a mixture of levobunolol hydrochloride and $PGF_{2\alpha}$-1-isopropyl ester dissolved in an ophthalmically compatible carrier, so as to reduce the intraocular pressure of the eye and maintain such reduced intraocular pressure.

This invention further provides a composition for the topical treatment of ocular hypertension or glaucoma which comprises an effective intraocular pressure reducing amount of a mixture of levobunolol hydrochloride and $PGF_{2\alpha}$-1-isopropyl ester dissolved in an ophthalmically compatible carrier.

DETAILED DESCRIPTION OF THE INVENTION

Figure 1:
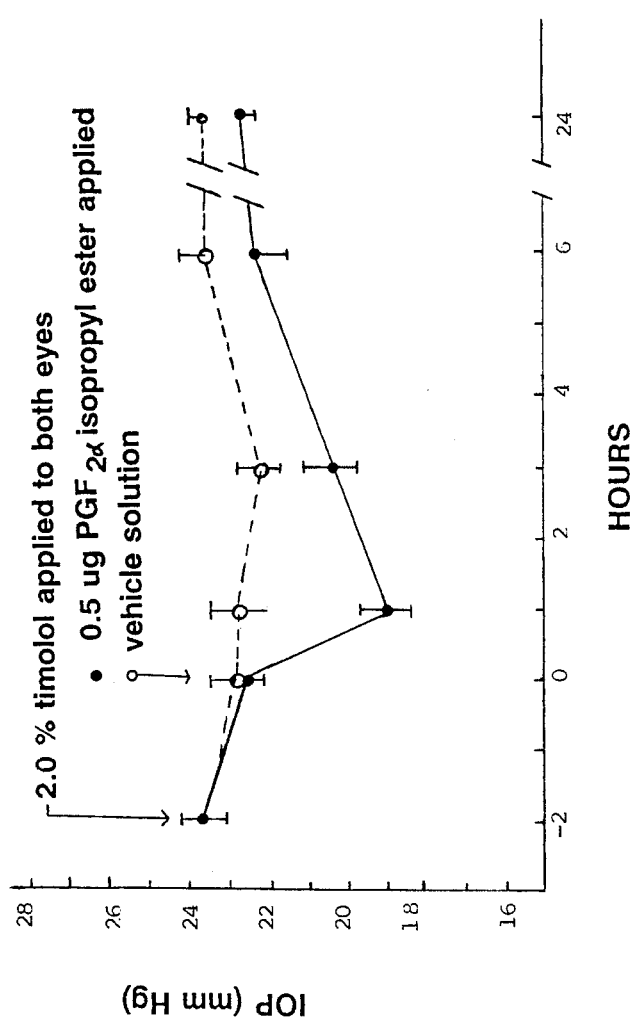
FIG. 1 This figure shows the effect of a 2% timolol solution and a combination of a 2% timolol solution and 0.5 g $PGF_{2\alpha}$-1-isopropyl ester on the intraocular pressure in cat eyes. Application of 0.5 $\mu$g $PGF_{2\alpha}$-1-isopropyl ester to eyes already treated with a 2% timolol solution caused a significant further drop in intraocular pressure within one hour.

This invention provides a method for treating ocular hypertension or glaucoma in a subject's eye. The method comprises contacting the surface of the eye with a composition comprising an effective intraocular pressure reducing amount of a mixture of an adrenergic blocking agent and a prostaglandin or prostaglandin derivative in an ophthalmically compatible carrier, so as to reduce the intraocular pressure of the eye and maintain such reduced intraocular pressure. In the preferred embodiment, the subject is a primate, particularly a human being.

Although any adrenergic blocking agent may be employed in the practice of this invention, the preferred adrenergic blocking agent is a beta blocker. The presently preferred beta blockers are timolol maleate, betaxolol hydrochloride, and levobunolol hydrochloride. Furthermore, while any prostaglandin or prostaglandin derivative may be employed in the practice of this invention, the presently preferred prostaglandin or prostaglandin derivative is of one of the A, E or F type. Of these types, $PGF_{2\alpha}$ or a $PGF_{2\alpha}$ derivative are particularly useful, specifically $PGF_{2\alpha}$-1-isopropyl ester.

Additionally, a range of concentrations of adrenergic blocking agents may be employed in the practice of the invention. However, the preferred amount present in the mixture is from about 0.01 $\mu$g to about 1,000 $\mu$g, specifically from about 5 $\mu$g to about 500 $\mu$g.

The presently preferred effective amount of prostaglandin or prostaglandin derivative present in the mixture is from about 0.01 $\mu$g to about 1,000 $\mu$g, specifically from about 0.1 $\mu$g to about 50 $\mu$g.

The ophthalmically compatible carrier may be any well known carrier. Presently preferred for use in the practice of this invention are aqueous solutions, such as a saline solution containing an ophthalmically compatible preservative a surfactant, and an agent, such as a soluble polymer, to increase the viscosity of the solution. In a preferred embodiment, the mixture is dissolved in the ophthalmically compatible carrier.

Various regimens may be employed for treating ocular hypertension or glaucoma in the subject's eye. In the preferred embodiment, the treatment comprises contacting the surface of the eye, i.e., the cornea, periodically, preferably at least daily, with an effective amount of a mixture of an adrenergic blocking agent and a prostaglandin or prostaglandin derivative to reduce intraocular pressure.

This invention further provides composition for topical treatment of ocular hypertension or glaucoma in a subject's eye. The composition comprises an effective intra-ocular pressure reducing amount of a mixture of an adrenergic blocking agent and a prostaglandin or a prostaglandin derivative in an ophthalmically compatible carrier.

In a preferred embodiment, the adrenergic blocking agent present in the composition is a beta blocker and the prostaglandin or prostaglandin derivative present in the composition is of the A, E or F type. The presently preferred beta blockers are timolol maleate, betaxolol hydrochloride, and levobunolol hydrochloride.

The presently preferred prostaglandin or prostaglandin derivative is $PGF_{2\alpha}$ or a $PGF_{2\alpha}$ derivative, specifically $PGF_{2\alpha}$-1-isopropyl ester.

The presently preferred effective amount of adrenergic blocking agent present in the composition is from about 0.01 $\mu$g to about 1,000 $\mu$g, specifically from about 5 $\mu$g to about 500 $\mu$g.

The presently preferred effective amount of prostaglandin or prostaglandin derivative present in the composition is from about 0.01 $\mu$g to about 1,000 $\mu$g, specifically from about 0.1 $\mu$g to about 50 $\mu$g.

The ophthalmically compatible carrier may be any well known carrier. Presently preferred for use in the practice of this invention are aqueous solutions, such as a saline solution containing an ophthalmically compatible preservative, a surfactant and an agent, such as a soluble polymer, to increase the viscosity of the solution. In a preferred embodiment, the mixture is dissolved in the ophthalmically compatible carrier.

This invention also provides a method for treating ocular hypertension or glaucoma in a primate subject's eye. The method comprises contacting the surface of the eye with a composition comprising an effective intraocular pressure reducing amount of a mixture of levobunolol and $PGF_{2\alpha}$-1-isopropyl ester dissolved in an ophthalmically compatible carrier, so as to reduce the intraocular pressure of the eye and maintain such reduced intraocular pressure.

This invention further provides a composition for the topical treatment of ocular hypertension or glaucoma comprising an effective intraocular pressure reducing amount of a mixture of levobunolol hydrochloride and $PGF_{2\alpha}$-1-isopropyl ester dissolved in an ophthalmically compatible carrier.

Finally, this invention provides a method for treating ocular hypertension or glaucoma in a subject's eye. The method comprises separately contacting the surface of the eye with an intraocular pressure reducing amount of an adrenergic blocking agent and of a prostaglandin or prostaglandin derivative, each in an ophthalmically compatible carrier, so as to reduce the intraocular pressure of the eye and maintain such reduced intraocular pressure.

EXPERIMENTAL RESULTS

Materials

The following materials used in the practice of this invention may be obtained from commercial sources: timolol maleate, (as Timoptic TM from Merck Sharp & Dohme Division of Merck & Co. Inc., West Point, Pa.), betaxolol hydrochloride (as Betoptic from Alcon Laboratories, Fort Worth, Tex.), and levobunolol HCl (as Betagan TM from Allergan America, Hormigueros, Puerto Rico).

Method

Trained, unanesthetized cats (1.5 to 3.0 kg) which showed on biomicroscopical evidence of ocular inflammation such as anterior chamber flare or cellular invasion were used in all experiments. Eight cats were used in each set of experiments. Intraocular pressures (IOP) were measured using an Alcon floating tip Applanation Pheumatonograph. The horizontal width of the pupil was measured using a millimeter pupil gauge. IOP and pupil diameters were measured before and several times after drug applications. Biomicroscopical examination of the anterior chamber was performed before and at 3, 6 and 24 hours after PG application.

$PGF_{2\alpha}$-1-isopropyl ester ($PGF_{2\alpha}$-IE) was supplied by Pharmacia AG (Uppsala, Sweden) already dissolved in 0.5% polysorbate 80 in normal saline containing 0.01% benzalkonium chloride; all dilutions were made up in this vehicle solution.

Timolol maleate powder was from Merck, Sharp and Dohme (West Point, Pa.) and was dissolved in 0.5% polysorbate 80 in normal saline with 0.01% benzalkonium chloride (40 mg/ml, and 20 mg/ml, respectively). Betaxolol hydrochloride (Betoptic; Alcon, Fort Worth, Tex.) at a concentration of 0.5% (5 mg/ml) and levobunalol hydrochloride (Betagan; Allergan, Irvine, Calif.) at a concentration of 0.5% (5 mg/ml), were obtained from the pharmacy.

In most experiments (those shown in FIGS. 1, 3 and 4), one beta-adrenergic blocking agents (500 µg Betoptic, or 125 µg Betagan) in a volume of 25 µl was applied first to both eyes of each cat immediately after baseline IOP and pupil diameter measurements. After 2 hours, immediately following another IOP and pupil diameter measurement, 0.5 µg (0.2%) of $PGF_{2\alpha}$-IE in a volume of 25 µl was applied to one eye of each cat while the contralateral eye received 25 µl of the vehicle solution. IOP and pupil diameter measurements along with biomicroscopic examination of the anterior chamber were performed as described above.

In one group of 8 cats (results shown in FIG. 2), a 25 µl-aliquot of a mixture of equal volumes of 4% timolol and 0.4% $PGF_{2\alpha}$-IE yielding a dose of 500 µg of timolol and 0.5 µg of $PGF_{2\alpha}$-IE in each 25 µl of 2% timolol (500 µg). IOP and pupil diameter measurements were taken as above.

Discussion

The beta blocker, timolol maleate, did not block the ocular hypotensive effect of $PGF_{2\alpha}$-1-isopropyl ester. As shown in FIG. 1, when a 2% timolol solution made up in an appropriate aqueous vehicle, was applied to both eyes of cats, there was some intraocular pressure reduction in both eyes at 2 hours. However, in the eyes which were then treated with 0.5 µg of $PGF_{2\alpha}$-1-isopropyl ester (which is a threshold ocular hypotensive dose of $PGF_{2\alpha}$ in this species), a highly significant further drop in intraocular pressure occured within one hour. In the contralateral eyes that received only timolol 2 hours earlier, the intraocular pressure only showed a very small, further decrease as compared to the pressure decrease observed during the first 2 hours.

Figure 2:
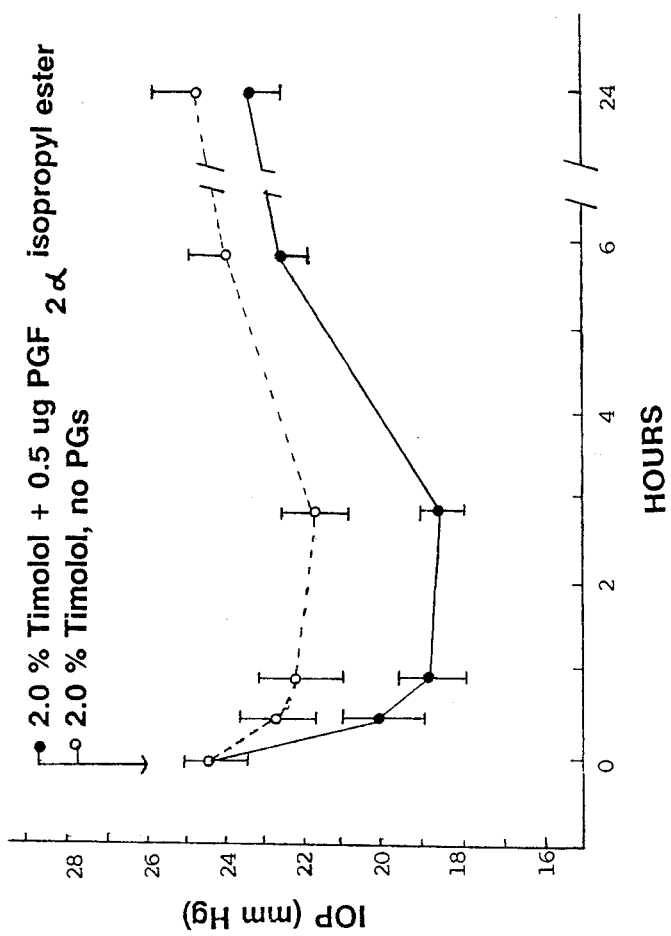
FIG. 2 This figure shows the ocular hypotensive effect of a solution containing both timolol (at a concentration of 2.0%) and $PGF_{2\alpha}$-1-isolpropyl ester (at a final concentration of 0.002%) on cat eyes as compared to the ocular hypotensive effect of timolol applied by itself.

Furthermore, as shown in FIG. 2, there was a significant pressure reduction in cat eyes that were treated with 25 µl of the vehicle solution containing both timolol maleate (at a final concentration of 2.0%) and $PGF_{2\alpha}$-1-isopropyl ester (at a final concentration of 0.002%) as compared to eyes that were treated with an identical volume of solution containing only timolol maleate. It should be noted that adrenergic receptors in cats have the same characteristics as other species, and, therefore, timolol maleate must be regarded as an adrenergic blocking agent in that species. Timolol maleate, however, is well-known to be a less effective pressure-reducing agent in cats than in humans. Therefore, in the human, the combination of timolol and a PG must have a greater effect than in cats. Since timolol maleate in the human, as in cats, acts by reducing the rate of aqueous humor production, while PG acts by increasing uveoscleral outflow, as long as timolol does not block the relaxing effect of PGs on the ciliary muscle, the effects of these two drugs must be at least additive.

Figure 3:
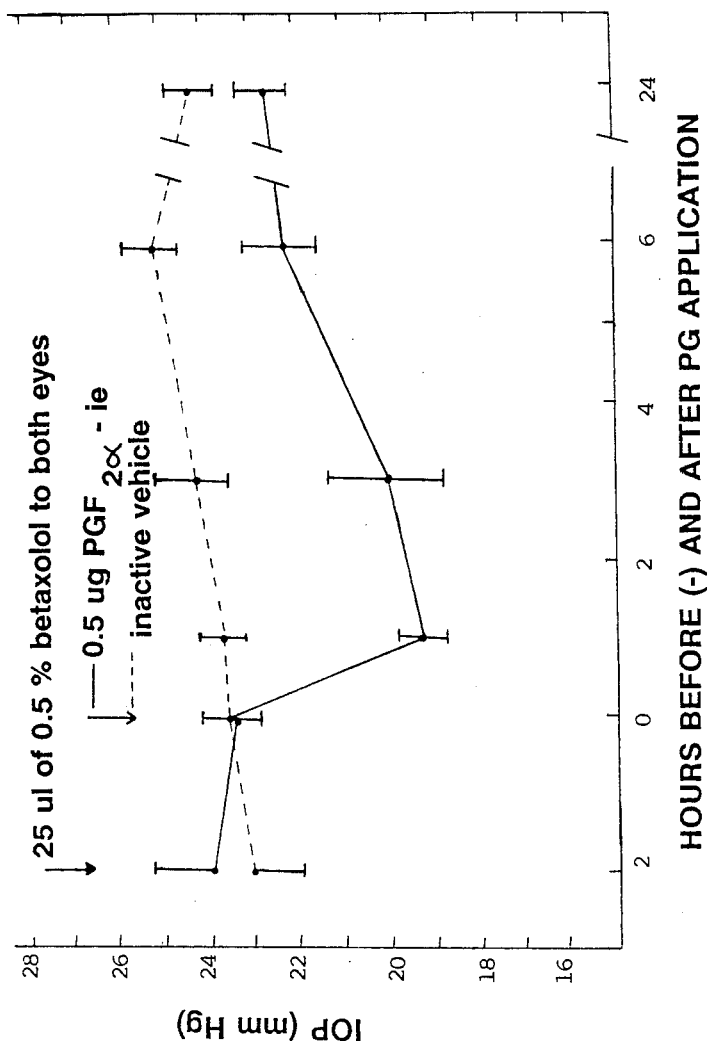
FIG. 3 This figure shows the ocular hypotensive effect of $PGF_{2\alpha}$-1-isopropyl ester on cat eyes pretreated 2 hrs earlier with an 0.5% solution of betaxolol.
Figure 4:
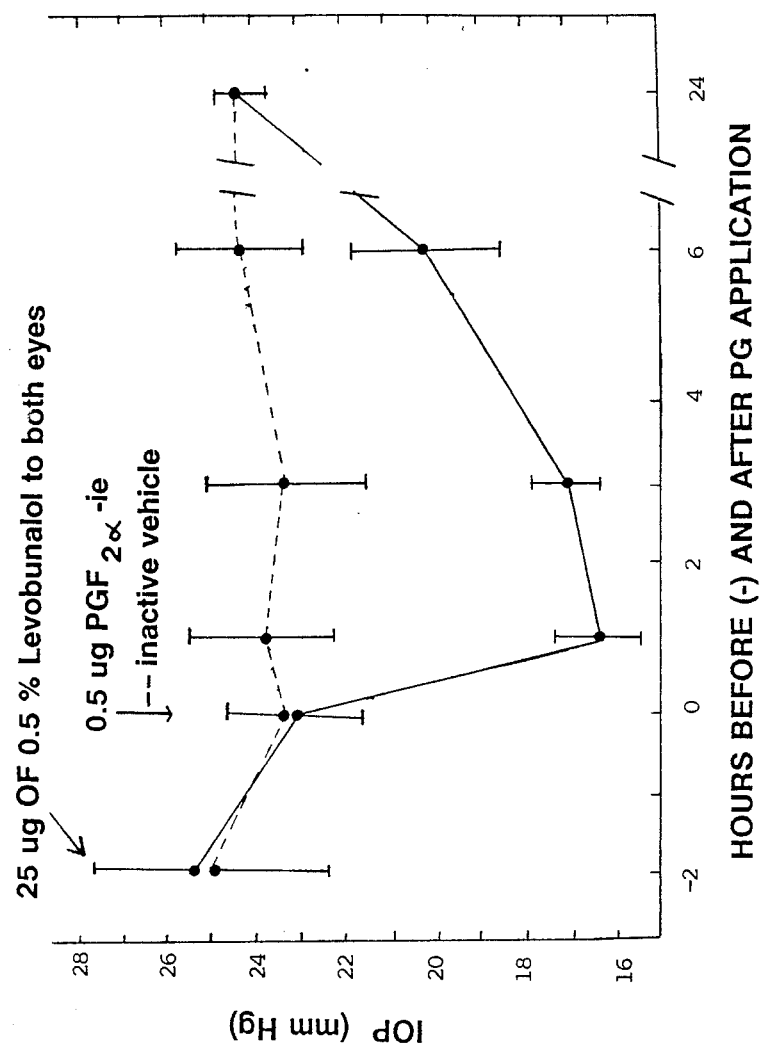
FIG. 4 This figure shows the ocular hypotensive effect of $PGF_{2\alpha}$-1-isopropyl ester on cat eyes pretreated 2 hrs earlier with an 0.5% solution of levobunolol.

Betaxolol hydrochloride and levobunolol hydrochloride also were employed in the practice of this invention, using 25 µl of the 0.5% clinically used solutions of Betoptic ® and Betagen ®, respectively. As is shown in FIG. 3 and FIG. 4, neither betaxolol hydrochloride nor levobunolol hydrochloride blocked the ocular hypotensive effect of $PGF_{2\alpha}$-1-isopropyl ester. This suggests that levobunolol hydrochloride may be a very good candidate for combined therapy, since there was a more pronounced reduction of intraocular pressure within one hour after the topical application of 0.5 µg of $PGF_{2\alpha}$-1-isopropyl ester in eyes that were pretreated with this beta blocker than typically occurs with this dose of $PGF_{2\alpha}$-1-isopropyl ester. See, for example, the much smaller ocular hypotensive response to this dose of $PGF_{2\alpha}$-1-isopropyl ester in betaxolol hydrochloride pretreated eyes (FIG. 3) as compared to levobunolol hydrochloride pretreated eyes (FIG. 4).

The positive interaction between levobunolol hydrochloride and $PGF_{2\alpha}$-1-isopropyl ester suggests that $PGF_{2\alpha}$-1-isopropyl ester may yield an effective intraocular pressure reduction at $PGF_{2\alpha}$-1-isopropyl ester doses even less than 0.5 μg. While 0.5 μg is already a very small dose of $PGF_{2\alpha}$-1-isopropyl ester, a further reduction in this dose may have important clinical significance, since studies of Alm and Villumsen (Proceeding of the International Society for Eye Research, Vol. IV, #18:15, Seventh International Congress of Eye Research, Nagoya, Japan 1986) on human eyes show that reduction of the $PGF_{2\alpha}$-1-isopropyl ester dose from 2.5 μg to 0.5 μg is sufficient to cause a considerable reduction in side effects, primarily conjunctival hyperemia. Therefore, the reduction of the $PGF_{2\alpha}$-1-isopropyl ester dose in a combined therapy with levobunolol, or some other beta blocker will yield a significant reduction of the undesirable side effects of $PGF_{2\alpha}$-1-isopropyl ester.

What is claimed is:

1. A method for treating ocular hypertension or glaucoma in a subject's eye which comprises contacting the surface of the eye with a composition comprising a beta-adrenergic blocking agent and an ester of prostaglandin $F_{2\alpha}$ or a derivative of an ester of prostaglandin $F_{2\alpha}$ in an ophthalmically compatible carrier, the amounts in the mixture being between about 5 μg and about 500 μg and between about 0.01 μg and about 1000 μg, respectively, and being such as to be effective so as to reduce the intraocular pressure of the eye and maintain such reduced pressure.

2. The method of claim 1, wherein the beta-adrenergic blocking agent is timolol maleate.

3. The method of claim 1, wherein the beta-adrenergic blocking agent is betaxolol hydrochloride.

4. The method of claim 1, wherein the beta-adrenergic blocking agent is levobunolol hydrochloride.

5. The method of claim 1, wherein the $PGF_{2\alpha}$ derivative is $PGF_{2\alpha}$-1-isopropyl ester.

6. A method of claim 1, wherein the prostaglandin $F_{2\alpha}$ or derivative of prostaglandin $F_{2\alpha}$ is present in the mixture in an amount between about 0.1 μg and about 500 μg.

7. A method of claim 1, wherein the ophthalmically compatible carrier comprises an aqueous solution.

8. A method of claim 7, wherein the aqueous solution is a saline solution containing an ophthalmically compatible preservative, a surfactant, and an agent, such as a soluble polymer, to increase the viscosity of the solution.

9. A method of claim 1, wherein the mixture is dissolved in the ophthalmically compatible carrier.

10. A method of claim 1, wherein the contacting is effected periodically.

11. A method of claim 10, wherein the periodic contacting is effected at least daily.

12. A method of claim 1, wherein the subject is a primate.

13. A composition for the topical treatment of ocular hypertension or glaucoma comprising a mixture of a beta-adrenergic blocking agent and an ester of prostaglandin $F_{2\alpha}$ or a derivative of an ester of prostaglandin $F_{2\alpha}$ in an ophthalmically compatible carrier and the amounts in the mixture being between 5 μg and about 500 μg and between about 0.01 μg and about 1000 μg, respectively, being such as to be effective so as to reduce the intraocular pressure of the eye and maintain such reduced pressure.

14. A composition of claim 13, wherein the beta-adrenergic blocking agent is timolol maleate.

15. A composition of claim 13, wherein the beta-adrenergic blocking agent is betaxolol hydrochloride.

16. A composition of claim 13, wherein the beta-adrenergic blocking agent is levobunolol hydrochloride.

17. A composition of claim 13, wherein the $PGF_{2\alpha}$ derivative is $PGF_{2\alpha}$-1-isopropyl ester.

18. A composition of claim 13, wherein the prostaglandin or prostaglandin derivative is present in the mixture in an amount between about 0.1 μg and about 50 μg.

19. A composition of claim 13, wherein the ophthalmically compatible carrier comprises an aqueous solution.

20. A composition of claim 19, wherein the aqueous solution is a saline solution containing an ophthalmically compatible preservative, a surfactant, and an agent, such as a soluble polymer, to increase the viscosity of the solution.

21. A composition of claim 13, wherein the mixture is dissolved in the ophthalmically compatible carrier.

22. A method for treating ocular hypertension or glaucoma in a primate subject's eye which comprises contacting the surface of the eye with a composition comprising an effective intraocular pressure reducing amount of a mixture of levobunolol hydrochloride and $PGF_{2\alpha}$-1-isopropyl ester dissolved in an ophthalmically compatible carrier, so as to reduce the intraocular pressure of the eye and maintain such reduced intraocular pressure.

23. A composition for the topical treatment of ocular hypertension or glaucoma comprising an effective intraocular pressure reducing amount of a mixture of levobunolol hydrochloride and $PGF_{2\alpha}$-1-isopropyl ester dissolved in an ophthalmically compatible carrier.

* * * * *